United States Patent [19]

Kosley, Jr.

[11] Patent Number: 4,810,792

[45] Date of Patent: Mar. 7, 1989

[54] PIPERIDINE INTERMEDIATES

[75] Inventor: Raymond W. Kosley, Jr., Bridgewater, N.J.

[73] Assignee: Hoechst-Roussel Pharmaceuticals Inc., Somerville, N.J.

[21] Appl. No.: 231,929

[22] Filed: Aug. 15, 1988

Related U.S. Application Data

[62] Division of Ser. No. 6,035, Jan. 22, 1987, Pat. No. 4,788,201.

[51] Int. Cl.$^4$ .......................................... B07D 211/48
[52] U.S. Cl. ..................................... 546/207; 546/216
[58] Field of Search ................................ 546/207, 216

[56] References Cited

U.S. PATENT DOCUMENTS

| | | | |
|---|---|---|---|
| 3,476,762 | 11/1969 | Beil | 546/207 |
| 3,484,446 | 12/1969 | Beil et al. | 546/207 |
| 3,743,645 | 7/1973 | Helsley | 546/216 |
| 4,579,950 | 4/1986 | Kosley et al. | 546/216 |
| 4,695,637 | 9/1987 | Kosley et al. | 546/216 |

*Primary Examiner*—Robert T. Bond
*Attorney, Agent, or Firm*—Raymond Wittekind

[57] ABSTRACT

Novel 3-methylenespiro[benzofuran-2(3H),4'-piperidines, intermediates and processes for the preparation thereof and methods for reducing blood pressure utilizing the compounds and compositions thereof are disclosed.

18 Claims, No Drawings

PIPERIDINE INTERMEDIATES

This is a division, of application Ser. No. 006,035 filed Jan. 22, 1987 now U.S. Pat. No. 4,788,201.

The present invention relates to novel 3-methylenespiro[benzofuranpiperidines]. More particularly, the present invention relates to 3-methylenespiro[benzofuran-2(3H),4′-piperidines] of formula 1

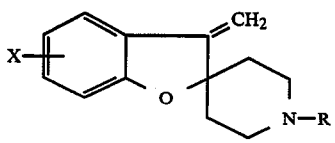

wherein R is hydrogen, loweralkyl, aralkyl, loweralkoxyloweralkyl, benzyloxyloweralkyl, a group of the formula

$COR^1$ wherein $R^1$ is aryl or loweralkyl; a group of the formula

$CR^2$ wherein $R^2$ is hydrogen or loweralkyl; a group of the formula

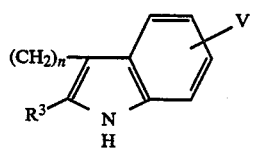

wherein $R^3$ is hydrogen or loweralkyl, V is hydrogen or halogen and n is 2, 3 or 4, a group of the formula

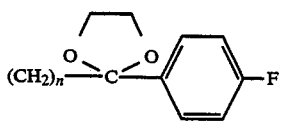

wherein n is 2 or 3, a group of the formula

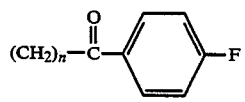

wherein n is 2 or 3, a group of the formula

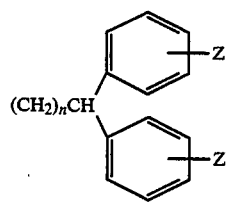

wherein Z is hydrogen, halogen, loweralkyl, loweralkoxy, trifluoromethyl or hydroxy and n is 1, 2, 3, or 4 or a group of the formula

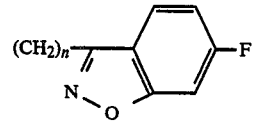

wherein n is 2, 3 or 4; X is hydrogen, halogen, loweralkyl, loweralkoxy, hydroxy or trifluoromethyl, an optical antipode thereof or a pharmaceutically acceptable acid addition salt thereof, which are useful as antihypertensive agents, alone or in combination with inert blood pressure reducing adjuvants, as well as intermediates and processes for the preparation thereof.

Preferred 3-methylenespiro[benzofuran]-2(3H),4′-piperidines of the present invention are those compounds wherein R is hydrogen, a group of the formula

$COR^1$, a group of the formula

$CR^2$, a group of the formula

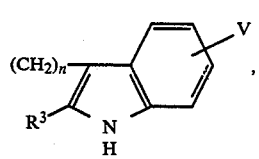

a group of the formula

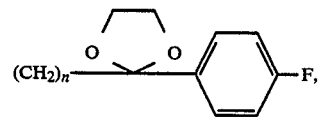

a group of the formula

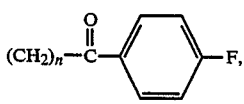

a group of the formula

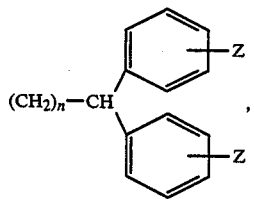

a group of the formula

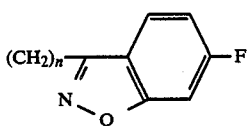

wherein $R^1$, $R^2$, $R^3$, V, Z and n are as defined hereinbefore.

The present invention also relates to 4-ethynyl-4-(2-nitrophenoxy)piperidines of formula 2

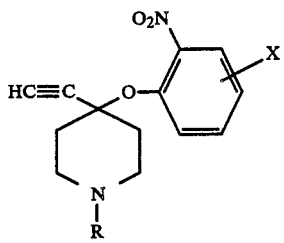

wherein R is hydrogen, loweralkyl, a group of the formula

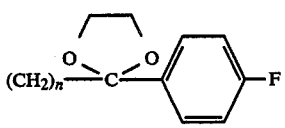

wherein n is 2 or 3, a group of the formula

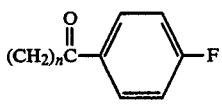

wherein n is 2 or 3, a group of the formula

COR$^1$ wherein $R^1$ is loweralkyl or phenyl or a group of the formula

CR$^2$ wherein $R^2$ is hydrogen or loweralkyl; and X is hydrogen, halogen, loweralkyl, loweralkoxy, hydroxy or trifluoromethyl, an optical isomer thereof or a salt thereof, and 4-ethylnyl-4-(2-aminophenoxy)-piperidines of formula 3

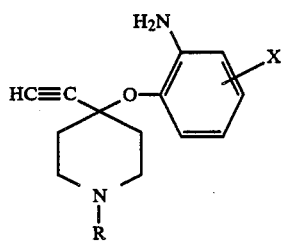

wherein R is loweralkyl, a group of the formula

COR$^1$ wherein $R^1$ is loweralkyl, or phenyl or a group of the formula

CR$^2$ wherein $R^2$ is hydrogen or lowerakyl; X is hydrogen, halogen, loweralkyl, loweralkoxy, hydroxy or trifluoromethyl, an optical antipode thereof and a salt thereof, useful as intermediates for the preparation of the hereinbeforementioned 3-methylenespiro [benzofuran-2(3H),4'-piperidines] of formula 1.

As used through the specification and appended claims, the term "alkyl" refers to a straight or branched chain hydrocarbon radical containing no unsaturation and having 1 to 10 carbon atoms such as methyl, ethyl, n-propyl, i-propyl, n-butyl, n-pentyl, i-pentyl, heptyl, octyl, decyl and the like. The term "alkoxy" refers to a monovalent substituent which consists of an alkyl group linked through an ether oxygen and having its free valence bond from the ether oxygen such as methoxy, ethoxy, i-propoxy, n-butoxy, tert-butoxy, n-pentoxy, i-pentoxy, heptoxy, hexoxy, octoxy, decoxy and the like. The term "alkanol" refers to a compound formed by combination of an alkyl group and hydroxy radical. Examples of alkanols are methanol, ethanol, n- and i-propanol, 2,2dimethylethanol, hexanol, octanol, decanol and the like. The term "alkanoic acid" refers to a compound formed by combination of a carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like. The term "alkanone" refers to a compound formed by replacement of the hydroxyl function of an alkanoic acid by an alkyl group. The term "halogen" refers to a member of the family fluorine, chlorine, bromine or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "aryl" refers to phenyl or phenyl substituted by one or more halogen, loweralkyl, loweralkoxy, hydroxy or trifluoromethyl groups. Examples of aryl functions are chlorophenyl, 1,2-dimethylphenyl, 1,3,5-trimethoxyphenyl, 1,3-dihydroxyphenyl, trifluorophenyl and the like. The term "aralkyl" refers to a group formed by combination of an aryl and an alkyl group. Examples of aralkyl groups include benzyl, 4-chlorophenylethyl, 3-(3,4-dimethylphenyl)pentyl, 1-(2,4,6-trimethoxyphenyl)propyl, 2-(3,5-dihydroxyphenylbutyl), 2-trifluoromethylphenyl ethyl and the like. The term "lower" as applied to any of the aformentioned groups refers to a group having a carbon skeleton containing up to and including 6 carbon atoms.

The compounds of the present invention which lack an element of symmetry exist as optical antipodes and as the racemic forms thereof. The optical antipodes may be prepared from the corresponding racemic forms by standard optical resolution techniques, involving, for example, the separation of diasteromeric salts of those compounds of the present invention characterized by the presence of a basic amino group and an optically active acid, or by the synthesis from optically active precursors.

The present invention comprehends all optical isomers and racemic forms thereof of the compounds disclosed and claimed herein and the formulas of the compounds shown herein are intended to encompass all possible tautomers and optical isomers of the compounds so depicted.

The novel 3-methylenespiro[benzofuran-2(3H),4'-piperidines] of the present invention are prepared from 4-ethynyl-4-hydroxypiperidines 4 by the processes illustrated in the Reaction Scheme.

To prepare the parent ring system 1, i.e. the 3-methylenespiro[benzofuran-2(3H),4'-piperidine] 1 wherein R is hydrogen, a 4-ethynyl-4-hydroxypiperidine 4 wherein R is loweralkyl or a group of the formula

CR² wherein R² is hydrogen or loweralkyl is condensed with a 2-fluoronitrobenzene 5 to provide a 4-ethynyl-4-(2-nitrophenoxy)piperidine 2 which is reduced to a 4-(2-aminophenoxy)-4-ethynylpiperidine 3, and cyclized to a spiro[benzofuranpiperidine] 1, from which the substitutent at the 1-position of the piperidine ring is cleaved.

The condensation is conveniently performed by contacting an ethynylcarbinol 4 with an alkali metal hydride in a polar aprotic solvent or combination thereof to form the alkali metal alkoxide salt of 4 followed by treatment of the alkoxide 4, so formed, with a 2-fluoronitrobenzene 5 to afford a phenoxypiperidine 2. Among alkali metal hydrides, there may be mentioned lithium hydride, sodium hydride and potassium hydride. Among dipolar aprotic solvents, there may be mentioned dimethylacetamide, dimethylformamide, hexamethylphosphoramide, dimethylsulfoxide. Sodium hydride is the preferred alkali metal hydride. Dimethylsulfoxide and mixtures of dimethylsulfoxides and hexamethylphosphoramide are the preferred solvent systems. The condensation temperature is not narrowly critical. It is preferred, however, to form the alkali metal alkali salt of 4 at a temperature within the range of about 60° to about 110°, most preferred within the range of about 80° to about 95°, and to conduct the etherification, i.e, the formation of 2 from the salt of 4 at a reduced temperature within the range of about −20° to about 40°, most preferred within the range of about 0° to 25°.

The reduction of a 4-ethynyl-4-(2-nitrophenoxy)-piperidine 2 wherein R is loweralkyl or a group of the formula

COR¹ wherein R¹ is loweralkyl or phenyl, a (2-aminophenoxy)-4-ethynylpiperidine 3 wherein R is loweralkyl or a group of the formula

COR¹ wherein R¹ is loweralkyl or phenyl is readily accomplished by treating a nitrophenoxypiperidine 2 with iron, preferably, electrolytically reduced iron, in the presence of a mineral acid such as hydrochloric acid, hydrobromic acid or sulfuric acid, preferably hydrochloric acid, in a solvent system comprising a loweralkanol and water, preferably methanol and water, at a reduction temperature, which although not crucial, of about 25° to 65°, preferably at about 45°.

The cyclization is achieved by contacting a 4-(2-aminophenoxy)piperidine 3 with an alkali metal nitrite in the presence of a mineral acid in water an or aqueous system containing a cosolvent at a noncritical reduced temperature followed by treatment of the diazonuim salt of a 4-(2-aminophenoxy)piperidine 3, so obtained, with hypophosphorous acid, also at a noncritical reduced temperature. Suitable alkali metal nitrites include lithium nitrite, sodium nitrite and potassium nitrite. Suitable mineral acids include hydrochloric acid, hydrobromic acid and sulfuric acid. Suitable aqueous solvent systems include aqueous alkanols and aqueous alkanones such as aqueous methanol or aqueous ethanol and aqueous acetones. The reduced temperature at which both steps of the cyclization process is performed is preferrably within the range of about −10° to 25°, most preferably at about 10°.

The cleavage of an alkanoylmethylenespiro[benzofuranpiperidine] 1 wherein R is

CR² wherein R² is alkyl or hydrogen is accomplished by conventional hydrolysis techniques. For example, treatment of 1-alkanoylpiperidine wherein R is

CR² wherein R² is alkyl or hydrogen with a mineral acid such as dilute sulfuric acid at ambient temperature yields a methylenespiro[benzofuranpiperidine] 1 unsubstituted at the 1-position of the piperidine ring, i.e., a compound of formula 1 wherein R is hydrogen.

The cleavage of an alkylmethylenespiro[benzofuranpiperidine] 1 wherein R is alkyl may also be accomplished by methods well known in the art. For example, treatment of a 1-alkylpiperidine 1 wherein R is alkyl with a chloroformate, such as phenyl chloroformate, may give a phenoxycarbonylpiperidine, i.e., a compound of formula 1 wherein R is

COR¹ wherein R¹ is phenyl, which may be hydrolyzed by an aqueous alkali metal hydroxide, such as aqueous sodium hydroxide, to yield an unsubstituted methylenespiro[benzofuranpiperidine] 1 wherein R is hydrogen.

Alternatively, to prepare a 3-methylenespiro[benzofuran-4'-piperidine] 1 wherein R is hydrogen, a 1- alkyl-4-ethynyl-4-(2-nitrophenoxy)piperidine 2 wherein R is alkyl is converted to a 1-alkoxy- or 1-phenyloxycarbonyl-4-ethynyl-4-(2-nitrophenoxy)piperidine 2 wherein R is a group of the formula

wherein $R^1$ is alkyl or phenyl which is reduced to a 1-alkoxy- or 1-phenyloxycarbonyl-4-ethynyl-4-(2-aminophenoxy)piperidine 3 by methods hereindescribed for the conversion of 2 to 3 and cyclized to a methylenespiro[benzofuranpiperidine] 1 wherein R is a group of the formula

wherein $R^1$ is alkyl or phenyl and subsequently cleaved to a methylenespiro[benzofuranpiperidine] 1 wherein R is hydrogen.

The conversion of a 1-alkylpiperidine 2 to a 1-alkoxy- or 1-phenyloxycarbonylpiperidine 2 is carried out under conventional conditions by treating a 1-alkylpiperidine 2 with an alkyl- or phenylchloroformate, optionally in the presence of an acid acceptor such as an alkali metal carbonate, for example, potassium carbonate, in a halocarbon or aromatic solvent such as dichloromethane or benzene at the reflux temperature of the reaction medium.

The cyclization of a 1-alkoxycarbonyl-4-(2-aminophenoxy)4-ethynylpiperidine 3 wherein R is a group of the formula

wherein $R^1$ is alkyl to a spiro[benzofuranpiperidine] 1 wherein R is a group of the formula

wherein $R^1$ is alkyl is achieved by the method hereinbeforedescribed for the conversion of a 4-aminophenoxypiperidine 3 wherein R is alkyl to a spiro[benzofuranpiperidine] 1 wherein R is alkyl. The cyclization of a 4-aminophenoxypiperidine 3 wherein R is a group of the formula

wherein $R^1$ is phenyl to a spiro[benzofuranpiperidine] 1 wherein R is a group of the formula

wherein R is phenyl may be achieved by substantially similar methods.

The cleavage of a methylenespiro[benzofuranpiperidine] 1 substituted at the 1-position of the piperidine ring by an alkoxycarbonyl or phenoxycarbonyl group may be achieved by conventional methods involving, for example, hydrolysis of the carbamate group with an alkali metal hydroxide, such as sodium hydroxide, in an aqueous alkanol, such as aqueous methanol, at ambient to the reflux temperature of the solvent system.

To prepare a methylenespiro[benzofuranpiperidine] having a (6-fluoro-1,2-benzisoxazol-3-yl)alkyl, a 4,4-bis(4-fluorophenyl)alkyl, or a (3-alkylindol-3-yl)alkyl group bound to the 1-position of the piperidine ring, a 1-unsubstituted methylenespiro[benzofuranpiperidine] 1 wherein R is H is condensed, respectively, with a 3-(ω-haloalkyl)-6-fluoro-1,2-benzisoxazole of formula 6

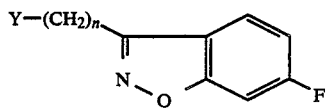

wherein Y is bromo or chloro and n is as above, a 4,4-bis-(4-fluorophenyl)alkyl halide of formula 7

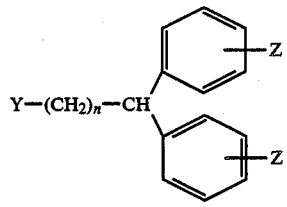

wherein Z is as hereinbeforedescribed, Y is chloro or bromo and n is as above, and a W-(phenylsulfonylalkyl)indole of formula 8

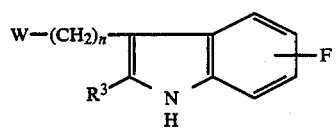

wherein $R^3$ is hydrogen or alkyl, W is benzenesulfonyl, and n is as above, the preparations of which are described in U.S. Pat. No. 4,352,811, granted Oct. 5, 1982, or may be accomplished by conventional methods.

The condensation of [benzofuranpiperidine]1 wherein R is hydrogen with halide 6 or 7 is readily performed by treating the N-unsubstituted piperidine 1 with a halide 6 or 7 in the presence of an acid acceptor, a displacement promoter and a suitable solvent. Among acid acceptors, there may be mentioned alkali metal carbonates and alkali metal bicarbonates such as, for example, sodium and potassium carbonate and sodium and potassium bicarbonate. Sodium bicarbonate and potassium carbonate are preferred. Among displacement promoters, there may be mentioned alkali metal halides such as, for example, sodium and potassium iodide, and sodium and potassium bromide. Potassium iodide is preferred. Among suitable solvents, there may be mentioned polar aprotic substances such as dimethylformamide, n-butylacetate, dimethylacetamide and hexamethylphosphoramide. Dimethylformamide is preferred. The temperature at which the condensation is conducted is not narrowly critical. It is desirable, however, to perform the reaction at a temperature within the range of about 50° C. to about 130° C. to assure a reasonable rate of conversion. A reaction temperature within the range of about 80° to 90° is preferred.

The reaction involving the displacement of the phenylfulfonyl group of 8 is accomplished by treating an N-unsubstituted piperidine 1 with a sulfonyl compound 8 in an aprotic polar solvent, such as dimethylformamide, n-butylacetate, dimethylacetamide and hexamethylphosphoramide, or in an alkanone such as acetone, 2-butanone, 3-pentanone and the like, dimethylformamide and 2-butanone being preferred, in the presence of an acid scavenger such as an alkali metal carbonate (sodium or potassium carbonate) or alkali metal bicarbonate (sodium or potassium carbonate) or alkali metal bicarbonate (sodium or potassium bicarbonate), potassium carbonate an sodium bicarbonate being preferred, at a temperature of about 70° to about 110°, preferably at a temperature of 90° C. when an aprotic polar solvent is used, and at about the reflux temperature of the reaction system when an alkanol is employed as the solvent.

A methylenespiro[benzofuranpiperidine] 1 wherein R is a group of the formula

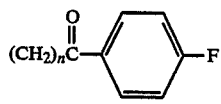

may be prepared by cyclizing a 4-(2-aminophenoxy)-4-ethynylpiperidine 3 wherein R is as above under conditions substantially the same as those described hereinbefore for the conversion of 3 to 1. The requisite aminophenoxyethynylpiperidine 3 may be obtained by reduction of a 4-(2-nitrophenoxy)-4-ethynylpiperidine 2 wherein R is as above according to the processes hereinbeforedescribed for the conversion of 2 to 3.

The intermediate 4-(2-nitrophenoxy)-4-ethynylpiperidine 2 wherein R is as immediately above is prepared by condensing a 4-(2-nitrophenoxy)-4-ethynylpiperidine 2 wherein R is hydrogen with a 4-fluorobenzoylalkyl halide etylene glycol ketal of formula 9

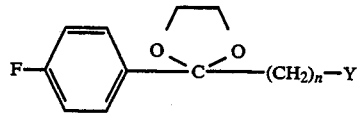

wherein Y is chloro or bromo and n is 2 or 3 in the presence of an acid acceptor such as, for example, potassium carbonate, a reaction promotor such as, for example, potassium iodide in an aprotric polar solvent such as, for example, dimethylformamide at the reflux temperature of the reaction medium to provide a 4-(2-nitrophenoxy)-4-ethynylpiperidine 2 wherein R is a group of the formula

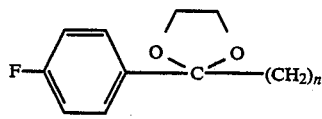

wherein n is 2 or 3 followed by hydrolysis of the ketal moiety by, for example, a mineral acid such as hydrochloric acid in an alkanol such as methanol at ambient temperature or an elevated temperature such as the reflux temperature of the solvent system.

4-Fluorobenzoylalkylhalide ethylene glycol ketals of formula 9 are synthesized by the processes disclosed in U.S. Pat. No. 4,352,811, granted Oct. 5, 1982.

The 3-methylenespiro[benzofuranpiperidines] of the present invention are useful as antihypertensives due to their ability to reduce blood pressure in mammals. Antihypertensive activity is measured in the spontaneous hypertensive rat by the indirect tail cuff method described by A. Schwartz, Ed., "Methods in Pharmacology," Vol. 1, Appleton-Centry-Crofts, New York, N. Y., 1971, page 135. According to this procedure, the test compound is administered orally to a group of 5 rats for 3 days in relation to a control group of the same number. The decrease in blood pressure is measured on the third day of administration. The antihypertensive activity expressed as the decrease in mean arterial blood pressure (mm of mercury) in this procedure of some of the compounds of the present invention is presented in the Table.

TABLE

| Compound | Dose (mg/kg of bodyweight) | Blood Pressure Decrease (mm/mercury) |
| --- | --- | --- |
| 1-N—[3-(3-methylindol-3-yl)propyl]-5-fluoro-3-methylenespiro[benzofuran-2(3H)—4'-piperidine] | 50 | 28 |
| 1-N—[4,4-bis(4-fluorophenyl)butyl]-5-fluoro-3-methylenespiro[benzofuran-2(3H)—4'-piperidine] | 50 | 78 |

Compounds of the invention also include:
(a) 5-fluoro-1-N-methyl-3-methylenespiro[benzofuran-2(3H),4'-piperidine];
(b) 5-fluoro-1-N-(2-methoxyethyl)-3-methylenespiro[benzofuran-2(3H),4'-piperidine];
(c) 5-fluoro-1-N-(2-benzyloxyethyl)-3-methylenespiro[benzofuran-2(3H),4'-piperidine];
(d) 5-methyl-1-N-methyl-3-methylenespiro[benzofuran-2(3H),4'-piperidine];
(e) 3-methylenespiro-5-methoxy[benzofuran-2(3H),4'-piperidine];
(f) 5-hydroxy-3-methylenespiro[benzofuran-2(3H),4'-piperidine];
(g) 5-trifluoromethyl-3-methylenespiro[benzofuran-2(3H),4'-piperidine];
(h) 1-N-[4,4-bisphenylbutyl]-5-fluoro-3-methylenespiro[benzofuran-2(3H),4'-piperidine];
(i) 1-N-[4,4-bis(2-ethylphenyl)propyl]-5-fluoro-3-methylenespiro[benzofuran-2(3H),4'-piperidine];
(j) 1-N-[4,4-bis(3-ethoxyphenyl)pentyl]-5-fluoro-3-methylenespiro[benzofuran-2(3H),4'-piperidine];
(k) 1-N-[4,4-bis(4-hydroxyphenyl)butyl]-5-fluoro-3-methylenespiro[benzofuran-2(3H),4'-piperidine];
(l) 1-N-[4,4-bis(4-trifluoromethylphenyl)butyl]-5-fluoro-3-methylenespiro[benzofuran-2(3H),4'-piperidine];
(m) 1-N-[3-(5-fluoro-2-methylindol-3-yl)propyl]-5-fluoro-3-methylenespiro[benzofuran-2(3H),4'-piperidine];
(n) N-formyl-3-methylenespiro[benzofuran-2(3H),4'-piperidine];
(o) 1-N-[3-(5-fluoroindol-3-yl)propyl]-3-methylenespiro[benzofuran-2(3H),4'-piperidine];

(p) 1-{N-3-[2-(4-fluorophenyl)-1,3-dioxolan-2-yl]propyl}5-fluoro-3-methylenespiro[benzofuran-2(3H),4'-piperidine]; and
(q) 1-[4-(4-fluorophenyl)-4-oxobutyl]-5-fluoro-3-methylenespiro[benzofuran-2(3H),4'-piperidine].

Additional compounds of the invention are:
(a) 4-ethynyl-4-(4-fluoro-2-nitrophenoxy)-1-formylpiperidine;
(b) 4-ethynyl-4-(4-methyl-2-nitrophenoxy)piperidine;
(c) 4-ethynyl-1-methyl-4-(4-methoxy-2-nitrophenoxy)piperidine;
(d) 1-acetyl-4-ethynyl-4-(4-hydroxy-2-nitrophenoxy)piperidine;
(e) 1-ethoxycarbonyl-4-ethynyl-4-(2-nitro-4-trifluoromethylphenoxy)piperidine;
(f) 4-(2-aminophenoxy)-4-ethynyl-1-formylpiperidine;
(g) 4-(2-amino-4-methylphenoxy)-4-ethynyl-1-methylpiperidine;
(h) 4-(2-amino-4-methoxyphenoxy)-4-ethynyl-1-methylpiperidine;
(i) 4-(2-amino-4-hydroxyphenoxy)-4-ethynyl-1-methylpiperidine; and
(j) 1-acetyl-4-(2-amino-4-trifluoromethylphenoxy)-4-ethynylpiperidine.

Blood pressure reduction is achieved when the present 3-methylenespiro[benzofuranpiperidine]s are administered to a subject requiring such treatment as an effective oral, parenteral or intravenous dose of from 0.01 to 100 mg/kg of body weight per day. A preferred effective dose within this range is from about 10 to about 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compounds. It is to be further understood that the dosages set forth herein are exemplary only and that they do not, to any extent, limit the scope or practce of the invention.

Effective amounts of the compounds of the invention may be administered to a subject by any one of various methods for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

The active compounds of the present invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to 75% of the weight of the unit. The amount of present compound in such composition is such that a suitable dosage will be obtained. Preferred compositions and preparations according to the present invention are prepared so that a oral dosage unit form contains between 1.0-300 mgs of active compound The tablets, pills, capsules, troches and the like may also contain the following ingredients: a binder such as microcrystalline cellulose, gum tragancanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit. For example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of the aforesaid compound, but may be varied between 0.5 and about 50% of the weight thereof. The amount of active compound in such compositions is such that a suitable dosage will be obtained. Preferred compositions and preparations according to the present invention are prepared so that a parenteral dosage unit contains between 0.5 to 100 mgs of the active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The following Examples are for illustrative purposes only and are not to be construed as limiting the invention. Temperatures are in degrees Centigrade (°C.).

EXAMPLE 1

1-Methyl-4-ethynyl-4-(2-nitrophenoxy)piperidine hydrochloride

A suspension of 0.58 g of sodium hydride (59% in oil; washed three times with hexanes) in 15 ml of dimethylsulfoxide was heated at 80°–90° for 0.5 hour under nitrogen. The resultant solution was cooled in an ice bath and 2.0 g of 1-methyl-4-ethynyl-4-hydroxypiperidine was added. After five min, the mixture was cooled to 0° and a solution of 2.4 g of 2-fluoronitrobenzene was added dropwise. The mixture was stirred 1 hr at 0°, 3 hrs at room temperature, poured into water, extracted twice with ether, washed with saturated sodium chloride solution and dried over anhydrous potassium carbonate. Filtration followed by evaporation of the solvent provided an oil, which was treated with ethereal hydrogen chloride to yield 2.34 g (54.8%) of product.

ANALYSIS: Calculated for $C_{14}H_{16}N_2O_3 \cdot HCl$: 56.66% C, 5.77% H, 9.44% N, Found 56.49% C, 5.76% H, 9.35% N.

EXAMPLE 2

1-Phenoxycarbonyl-4-ethynyl-4-(2-nitrophenoxy)-piperidine

To a solution of 1-methyl-4-ethynyl-4-(2-nitrophenoxy)piperidine (liberated from 10.0 g of the hydrochloride) in 45 ml of methylene chloride was added dropwise a solution of 5.8 g of phenylchloroformate in 45 ml of methylene chloride. The mixture was stirred at room temperature for 1 hr and at reflux, under nitrogen, for 16 hrs. The solution was allowed to cool to room temperature, poured into water, extracted with methylene chloride, washed with saturated sodium chloride solution and dried over anhydrous potassium carbonate. Filtration followed by evaporation of solvent provided an oil (13.9 g). A 2.2 g sample of the oil was chromatographed on 150 g of alumina. The column was eluted with three 150 ml volumes of ether. Evaporation of the solvent from the second fraction provided 1.36 g (65%) of product. Recrystallization from isopropyl alcohol provided the analytical sample, mp 76°–80°.

ANALYSIS: Calculated for $C_{20}H_{18}N_2O_5$: 65.56% C, 4.95% H, 7.65% N, Found: 65.40% C, 4.98% H, 7.66% N.

EXAMPLE 3

4-Ethynyl-4-(2-nitrophenoxy)piperidine maleate

A suspension of 1.00 g of 1-phenoxycarbonyl-4-ethynyl-4-(2-nitrophenoxy)piperidine, 14 ml of methanol, and 6 ml of 15% sodium hydroxide solution was heated at reflux for 2.5 hrs under nitrogen and allowed to cool to room temperature. The mixture was poured into water, extracted twice with chloroform, washed with saturated sodium chloride solution and dried over anhydrous potassium carbonate. Evaporation of solvent provided an oil. Treatment of a solution of the oil with ethereal maleic acid provided 0.43 g (43%) of product, mp 155°–157°.

ANALYSIS: Calculated for $C_{13}H_{14}N_2O_3 \cdot C_4H_4O_4$: 56.35% C, 5.01% H, 7.73% N, Found: 56.34% C, 5.01% H, 7.81% N.

EXAMPLE 4

1-Acetyl-4-ethynyl-4-(2-nitrophenoxy)piperidine

To a stirred solution of dimsyl sodium, prepared from 16.5 g of sodium hydride (50% in oil, washed three times with hexanes) and 400 ml of dimethylsulfoxide at 17°–25° was added, in aliquots, 57.7 g of 1-acetyl-4-ethynyl-4-piperidinol. Upon completion of the addition, 55.3 g of 2-fluoronitrobenzene was added dropwise at a rate such that the temperature remained below 25°. The mixture was stirred at room temperature for 20 min, poured into cold water, extracted three times with ether, washed with saturated sodium chloride solution and dried over anhydrous potassium carbonate. Filtration followed by evaporation of solvent provided an oil, which crystallized on standing. Recrystallization from ethyl acetate/cyclohexane provided 23.6 g (24%) of product, mp 112°–115°.

ANALYSIS Calculated for $C_{15}H_{16}N_2O_4$: 62.49% C, 5.59% H, 9.72% N, Found: 62.26% C, 5.60% H, 9.59% N.

EXAMPLE 5

1-Methyl-4-(2-aminophenoxy)-4-ethynylpiperidine

A suspension of 1-methyl-4-ethynyl-4-(2-nitrophenoxy)piperidine (liberated from 10.0 g of the hydrochloride), 140 ml of methanol, 40 ml of water, 10 ml of conc hydrochloric acid and 20 g of iron (reduced electroytic) was stirred for 0.5 hr at 45° under nitrogen. The mixture was allowed to cool to room temperature, poured into saturated sodium carbonate solution, extracted twice with ether; dried over anhydrous potassium carbonate, filtered, and the solvent was evaporated to provide an oil. The oil was dissolved in ether. Precipitation with ethereal hydrogen chloride provided 8.59 g (83%) of product. Recrystallization from ethanol provided the analytical sample.

ANALYSIS Calculated for $C_{14}H_{19}N_2O \cdot 2HCl$: 55.45% C, 6.65% H, 9.24% N, Found: 55.76% C, 6.76% H, 9.18% N.

EXAMPLE 6

N-Methyl-4-ethynyl-4-(4-fluoro-2-nitrophenoxy)piperidine

To a stirred solution of dimsyl sodium prepared from 43.0 g of sodium hydride (50% in oil, washed three times with hexanes) and 1100 ml of dimethylsulfoxide was added, in aliquots, 125 g of N-methyl-4-ethynyl-4-piperidinol at a rate such that the temperature remained below 23°. When the addition was complete, 167 g of 2,5-difluoronitrobenzene was added slowly dropwise at a rate such that the temperature remained below 21°. When the addition was complete, the mixture was poured into ice, extracted twice with ether, washed with saturated sodium chloride solution, and dried over anhydrous magnesium sulfate. The mixture was filtered and the filtrate was concentrated. The residue was filtered through 800 g of silica gel (70–250 mesh) and eluted with 3 l of 10% methanol/dichloromethane. Evaporation of solvent provided an oil, which crystallized on standing to yield 134 g (54%) of product. Recrystallization from cyclohexane provided the analytical sample, mp 70°–73°.

ANALYSIS Calculated for $C_{14}H_{15}FN_2O_3$: 60.42% C, 5.43% H, 10.07% N, Found: 60.27% C, 5.43% H, 10.04% N.

EXAMPLE 7

1-N-Ethoxycarbonyl-4-ethynyl-4-(4-fluoro-2-nitrophenoxy)piperidine

A suspension of 223 g of N-methyl-4-ethynyl-4-(4-fluoro-2-nitrophenoxy)piperidine, 2 l of dry benzene, 165 g of anhydrous potassium carbonate and 130.3 g of ethyl chloroformate was stirred at reflux for 18 hr under nitrogen. The mixture was filtered and the solvent evaporated. The residue was dissolved in ether, washed with hydrochloric acid, saturated sodium bicarbonate solution, water and saturated sodium chloride solution. The ether solution was dried over anhydrous sodium sulfate and filtered. Evaporation of solvent provided an oil, which was dried at 50°–55° (1 mm). The oil crystallized to provide 226 g (83.8%) of product, mp 56°–68°.

ANALYSIS Calculated for $C_{16}H_{17}FN_2O_5$: 57.14% C, 5.10% H, 8.33% N, Found: 57.30% C, 5.12% H, 8.17% N.

EXAMPLE 8

1-N-Phenoxycarbonyl-4-ethynyl-4-(4-fluoro-2-nitrophenoxy)piperidine

To a stirred suspension of 5.01 g of potassium carbonate, 50 ml of dichloromethane (dried over anhydrous magnesium sulfate) and 10.1 g of 1-N-methyl-4-ethynyl-4-(4-fluoro-2-nitrophenoxy)piperidine was added dropwise a solution of 5.66 g of phenylchloroformate in 50 ml of dichloromethane (dried over anhydrous magnesium sulfate). The mixture was stirred 12 hr at ambient temperature and 6 hr at reflux under nitrogen. The suspension was poured onto ice, extracted with dichloromethane, washed with 15% sodium hydroxide solution, 1N hydrochloric acid and saturated sodium chloride solution. The dichloromethane solution was dried over anhydrous sodium sulfate, filtered and the solvent evaporated to provide an oil. The oil was dissolved in ether, washed with water, 1N hydrochloric acid and saturated sodium chloride solution. The solution was dried over anhydrous sodium sulfate, filtered and the solvent evaporated to provide an oil. The oil was dried overnight at room temperature (1 mm) during which time it crystallized to provide 10.3 g (73.8%) of product. Recrystallization from cyclohexane/ethyl acetate provided the analytical sample, mp 82°–83°.

ANALYSIS Calculated for $C_{20}H_{17}FN_2O_5$: 62.49% C, 4.46% H, 7.29% N, Found: 62.43% C, 4.50% H, 7.11% N.

EXAMPLE 9

1-N-Ethoxycarbonyl-4-(2-amino-4-fluorophenoxy)-4-ethynylpiperidine

To a stirred solution of 22.3 g of 1-ethoxycarbonyl-4-ethynyl-4-(4-fluoro-2-nitrophenoxy)piperidine in 535 methanol was added 37 ml of concentrated hydrochloric acid in 150 ml of water. To the stirred mixture was added 78.6 g of iron (reduced, electrolytic) in aliquots. The reaction temperature rose to 45°. The reaction mixture cooled to ambient temperature over 1.5 hr. The mixture was poured into water/ice/sodium carbonate solution, extracted with dichloromethane, washed with water and saturated sodium chloride solution and dried over anhydrous potassium carbonate. Filtration followed by evaporation of solvent provided 20.2 g of an oil. An aliquot of 10.0 g of the oil was dissolved in ether and filtered through 200 g of alumina and the filtrate was evaporated. The residue was dissolved in 10% methanol/dichloromethane, filtered through 200 g of silica gel, and the filtrate was evaporated to provide 8.6 g (84.7%) of product, as an oil.

ANALYSIS: Calculated for $C_{16}H_{19}FN_2O_3$: 62.73% C, 6.25% H, 9.15% N, Found 62.92% C, 6.23% H, 9.17% N.

EXAMPLE 10

1'-N-Ethoxycarbonyl-5-fluoro-3-methylenespiro[benzofuran-2(3H)-4'-piperidine]

To a stirred solution of 143 g of 1-N-ethoxycarbonyl-4-ethynyl-4-(2-amino-4-fluorophenoxy)piperidine in 375 ml of acetone was added a solution of 50 ml of concentrated hydrochloric acid in 375 ml of water. The mixture was cooled to below 10° and 54 ml of concentrated hydrochloric acid was added dropwise at a rate such that the temperature remained below 10°. To the mixture was then added, dropwise, a solution of 36.1 g sodium nitrite in 78 ml of water at a rate such that the temperature remained below 10°. The mixture was subsequently stirred ½ hr at 0°–10 ° and filtered into a stirred solution of 1025 ml of 30% hypophosphorous acid, maintained below 15°. The mixture was stirred 3 min and 1 l of ether was added. The mixture was stirred 8 hr in an ice-bath and allowed to warm to room temperature overnight. The ether layer was separated and the aqueous layer extracted with ether. The combined ether solutions were washed with water, saturated sodium chloride solution and dried over anhydrous potassium carbonate. The mixture was filtered and the filtrate was evaporated. The residue was dissolved in ether and filtered through 650 g of alumina (eluent: 2 l of ether). Evaporation of the solvent from the filtrate provided an oil. The oil was purified by high pressure liquid chromatography on a Waters Prep 500 instrument using two 500-cc silica gel columns (eluent: 0.25% methanol/dichloromethane). Evaporation of solvent from the appropriate fractions provided 22.0 g (16%) of product, which crystallized after drying overnight at 1 mm. Recrystallization from hexane provided the analytical sample, mp 80°–85°.

ANALYSIS: Calculated for $C_{16}H_{18}FNO_3$: 65.97% C, 6.23% H, 4.81% N, Found: 65.70% C, 6.04% H, 4.84% N.

EXAMPLE 11

1-N-Phenoxycarbonyl-4-(2-amino-4-fluorophenoxy)-4-ethynylpiperidine

To a stirred suspension of 735 ml of methanol and 51.7 g of 1-N-phenoxycarbonyl-4-ethynyl-4-(4-fluoro-2-nitrophenoxy)piperidine was added a solution of 51 ml of concentrated hydrochloric acid in 206 ml of water. To the stirred mixture was added, in aliquots, 80.2 g of iron (reduced, electrolytic). The mixture was stirred 2 hr, heated to 45° for 1 hr and allowed to cool to room temperature. The mixture was poured into ice/water, extracted twice with dichloromethane, washed with saturated sodium chloride solution and dried over anhydrous potassium carbonate. The mixture was filtered and the filtrate was evaporated. The residue was purified by chromatography on a Waters Prep 500 High Pressure Liquid Chromatograph (1×500 cc silica gel: eluent: 0.5 methanol/dichloromethane). Concentration of the appropriate fractions provided an oil, which crystallized on standing to provide 15.7 g (33%) of product. Recrystallization from cyclohexane/ethyl acetate provided the analytical sample, mp 125°–127°.

ANALYSIS: Calculated for $C_{20}H_{19}FN_2O_3$: 67.78% C, 5.40% H, 7.91% N, Found: 67.83% C, 5.38% H, 7.75% N.

EXAMPLE 12

1-Acetyl-4-ethynyl-4-(4-fluoro-2-nitrophenoxy)piperidine

A solution of dimsyl sodium was prepared by stirring 70 ml of dimethylsulfoxide and 2.57 g of sodium hydride at 80°–95° until the sodium hydride dissolved and evolution of hydrogen ceased. The solution was then cooled in an ice-bath to 20° and 3.5 ml of hexamethylphosphoramide was added. The solution was cooled to below 15° and 10 g of 1-acetyl-4-ethynyl-4-piperidinol was added in aliquots at a rate such that the temperature remained at 15°–20°. To the mixture was added dropwise 10.9 g of 2,5-difluoronitrobenzene at a rate such that the temperature remained at 15°–20°. When the addition was complete, the mixture was allowed to warm to ambient temperature, stirred ½ hr and poured onto ice. The mixture was extracted twice with ether, washed with saturated sodium chloride solution and dried over anhydrous magnesium sulfate. The mixture was filtered and the filtrate was evaporated. The residue was dissolved in 10% methanol/dichloromethane, filtered through 200 g of silica gel and eluted with 500 ml of 10% methanol/dichloromethane. Evaporation of solvent provided an oil, which crystallized. Recrystallization from ethyl acetate/cyclohexane provided 6.42 g (40%) of product, mp 111°–113°.

ANALYSIS Calculated for $C_{15}H_{15}FN_2O_4$: 58.82% C, 4.94% H, 9.15% N, Found: 59.14% C, 4.94% H, 9.05% N.

EXAMPLE 13

1-Acetyl-4-(2-amino-4-fluorophenoxy)-4-ethynylpiperidine hydrochloride

To a stirred solution of 3.14 g of 1-acetyl-4-ethynyl-4-(4-fluoro-2-nitrophenoxy)piperidine and 42 ml of methanol was added a solution of 3 ml of concentrated hydrochloric acid in 12 ml water. To the stirred mixture in a water bath was added 6.1 g of iron (powdered electrolytic) The mixture was stirred for 1 hr, poured into ice, made basic by the addition of sodium carbonate solution, extracted twice with methylene chloride and washed with saturated sodium chloride solution. The mixture was dried over anhydrous potassium carbonate, filtered and the solvent evaporated to provide an oil. The oil was purified on a Waters Prep 500 High Pressure Liquid Chromatograph instrument, using a silica gel column and eluting with 2% methanol/dichloromethane. The appropriate fractions were evaporated and the residue was treated with ethereal hydrogen chloride to provide 0.57 g (17.7%) of product, mp 206°–208°, after recrystallization from ethanol/methanol.

ANALYSIS Calculated for $C_{15}H_{17}FN_2O_2 \cdot HCl$: 57.60% C, 5.80% H, 8.96% N, Found: 57.70% C, 5.87% H, 8.99% N.

EXAMPLE 14

1'-N-Acetyl-5-fluoro-3-methylenespiro[benzofuran-2(3H),4'-piperidine]

A stirred suspension of 19.4 g of 1-N-acetyl-4-(2-amino-4-fluorophenoxy)-4-ethynylpiperidine, 91 ml of water and 6.9 ml of hydrochloric acid was heated at reflux until the starting material dissolved. The mixture was then cooled to below 10°. To the mixture was added slowly, dropwise, 7.6 ml of concentrated hydrochloric acid at a rate such that the temperature did not exceed 10°. To the mixture was then added dropwise a solution of 5.09 g of sodium nitrite in 11 ml water, maintaining the temperature below 10°. The mixture was stirred at 5°–10° for 25–30 min and subsequently filtered into 145 ml of 30% hypophosphorous acid. The mixture was allowed to stand overnight in a cold room and at room temperature for 8 hr. The mixture was diluted with water, extracted twice with ether, washed with saturate sodium chloride solution and dried over anhydrous magnesium sulfate. The mixture was filtered and the filtrate was evaporated. The residue was filtered through 200 g of alumina and eluted with 600 ml of ether. Evaporation of solvent provided an oil, which crystallized on standing to yield 4.72 g (25.7%) of product, mp 114°–116°.

ANALYSIS: Calculated for $C_{15}H_{16}NO_2F$: 68.94% C, 6.17% H, 5.36% N, Found: 68.94% C, 6.09% H, 5.27% N.

EXAMPLE 15

5-Fluoro-3-methylenespiro[benzofuran-2(3H),4'-piperidine]

A mixture of 5.0 g of 1'-acetyl-5-fluoromethylenespiro[benzofuran-2(3H),4'-piperidine] and 52 ml of 10% sulfuric acid was stirred at reflux for 1.75 hr and allowed to cool to room temperature. The mixture was slowly poured into ice/sodium carbonate solution/ether. The mixture was extracted twice with ether, washed with saturated sodium chloride solution and dried over anhydrous potassium carbonate. Filtration followed by evaporation of solvent provided an oil. Treatment of a solution of the oil in ether with oxalic acid in ether followed by recrystallization from methanol gave 2.08 g (35.2%) of product, mp 216°–217°.

ANALYSIS: Calculated for $C_{13}H_{14}FNO \cdot C_2H_2O_4$: 58.25% C, 5.22% H, 4.53% N, Found 58.07% C, 5.11% H, 4.50% N.

EXAMPLE 16

1'-N-[4,4-Bis(p-fluorophenyl)butyl]-5-fluoro-3-methylenespiro[benzofuran-2(3H)-4'-piperidine] oxalate A suspension of 5.23 g of 5-fluoro-3-methylenespirobenzofuran-2(3H)-4'-piperidine, 2.86 g of potassium carbonate, 33 ml of dimethylformamide, 0.57 g of potassium iodide and 7.28 g of bis(4-fluorophenyl)butyl chloride was stirred at 80°–85° under nitrogen for 2 hr. The mixture was poured into ice/ether, extracted twice with ether, washed with water, saturated sodium chloride solution and dried over anhydrous potassium carbonate. The mixture was filtered and the filtrate was evaporated. The residue was dissolved in ether and filtered through 200 g of alumina (eluent:ether). The ether solution was concentrated to provide an oil. The oil was dissolved in 10% methanol/dichloromethane and filtered through 200 g of silica gel (eluent: 800 m of 10% methanol/dichloromethane). The methanol/dichloromethane solution was concentrated to an oil. Treatment of the oil in ether with oxalic acid in ether, followed by recrystallization from isopropyl alcohol provided 3.05 g (23%) of product, mp 170°–175°.

ANALYSIS: Calculated for $C_{29}H_{28}NO \cdot C_2H_2O_4$: 67.26% C, 5.46% H, 2.53% N, Found: 66.91% C, 5.27% H, 2.85% N.

EXAMPLE 17

1'-N-[3'-(6-Fluoro-1,2-benzisoxazol-3-yl)propyl]-5-fluoro-3-methylenespiro[benzofuran-2(3H)-4'-piperidine] oxalate A suspension of 3.28 g of 5-fluoro-3-methylenespiro[benzofuran-2(3H)-4'-piperidine], 1.80 g of sodium bicarbonate, 21 ml of dimethylformamide, 0.4 g of potassium iodide, and 4.01 g of 3-(3'-chloropropyl)-1,2-benzisoxazole was stirred under nitrogen at 80°–90° for 2 hr. The mixture was allowed to cool to room temperature, poured into ice/saturated sodium carbonate solution/ether, extracted twice with ether and washed with saturated sodium chloride solution. The ether solution was dried over anhydrous potassium carbonate and filtered. The filtrate was evaporated. The residue was dissolved in ether and filtered through 150 g of alumina. The column was eluted with 300 ml ether. Evaporation of solvent provided an oil. Treatment of the oil in ether with oxalic acid in ether, followed by recrystallization from isopropyl alcohol provided 2.39 g (32.8%) of product, mp 75°–80°.

ANALYSIS: Calculated for $C_{23}H_{22}F_2N_2O_2$: 61.72% C, 4.97% H, 5.76% N, Found: 61.39% C, 5.00% H, 5.62% N.

EXAMPLE 18

1-N-[3-(2-Methylindol-3-yl)propyl]-5-fluoro-3-methylenespiro[benzofuran-2(3H)-4'-piperidine] oxalate A suspension of 4.2 g of 5-fluoro-3-methylenespiro[benzofuran-2(3H)-4'-piperidine], 2.30 g of sodium bicarbonate, 27 ml of dimethylformamide and 7.59 g 3-(benzenesulfonyloxy)propyl-2-methylindole was stirred at 80°–90° for 2 hr under nitrogen. The mixture was allowed to cool to room temperature, poured into ice-/water/ether, extracted twice with ether, washed with water, saturated sodium chloride solution and dried over anhydrous potassium carbonate. The mixture was filtered and the filtrate was evaporated. The residue was filtered through 90 g of silica gel (eluent: 10% methanol/dichloromethane). Evaporation of solvent provided an oil, which was filtered through alumina (eluent:ether). Evaporation of solvent followed by treatment of the residue with oxalic acid in ether and recrystallization from isopropyl alcohol provided 1.02 g (11%) of product, mp 93°–98°.

ANALYSIS Calculated for $C_{25}H_{27}FN_2O \cdot C_2H_2O_4$: 67.48% C, 6.08% H, 5.83% N, Found: 67.53% C, 6.10% H, 6.02% N.

EXAMPLE 19

1-{N-3-[2-(4-Fluorophenyl)-1,3-dioxolan-2-yl]propyl}-4-ethynyl-4(2-nitrophenoxy)piperidine oxalate A suspension of 4-ethynyl-4-(2-nitrophenoxy)piperidine liberated (methylene chloride/saturated sodium carbonate) from 10 g of the maleate salt, 9.5 g of potassium carbonate, 25 ml of dimethylformamide, 0.4 g of potassium iodide and 7.38 g of 2-[3-(chloropropyl)-2-(4-fluorophenyl]dioxolane was heated at reflux for 2.75 hrs and allowed to stand overnight. The mixture was diluted with water, extracted twice with ether, washed with saturated sodium chloride solution and dried over anhydrous potassium carbonate. Filtration followed by evaporation of solvent provided an oil. The oil was dissolved in ether and treated with ethereal oxalic acid to provide 9.27 g (62%) of product. Recrystallization from ethanol-methanol provided the analytical sample, mp 183°–185°.

ANALYSIS: Calculated for $C_{25}H_{27}FN_2O_5 \cdot C_2H_2O_4$: 59.55% C, 5.37% H, 5.15% N, Found 59.82% C, 5.24% H, 5.21% N.

EXAMPLE 20

1-[4-(4-Fluorophenyl)-4-oxobutyl]-4-ethynyl-4-(2-nitrophenoxy) piperidine hydrochloride A solution of 1-{N-3-[2-(4-fluorophenyl)-1,3-dioxolan-2-yl]propyl}-4-ethynyl-4-(2-nitrophenoxy)piperidine (liberated from 9.94 g of the oxalate salt), 60 ml of 3N hydrochloric acid and 150 ml of methanol was stirred at reflux for 2.5 hr under nitrogen and subsequently allowed to cool to room temperature. The mixture was poured into ice cold saturated sodium carbonate solution, extracted twice with ether, washed with saturated sodium chloride solution and dried over anhydrous magnesium sulfate. Filtration followed by evaporation of solvent provided an oil, which was dissolved in ether. Treatment with ethereal hydrogen chloride effected precipitation of a salt. Recrystallization of the salt provided 4.53 g (58.6%) of product, mp 168°–172°.

ANALYSIS: Calculated for $C_{23}H_{23}FN_2O_4 \cdot HCl$: 61.82% C, 5.41% H, 6.27% N, Found 61.94% C, 5.35% H, 6.22% N.

REACTION SCHEME

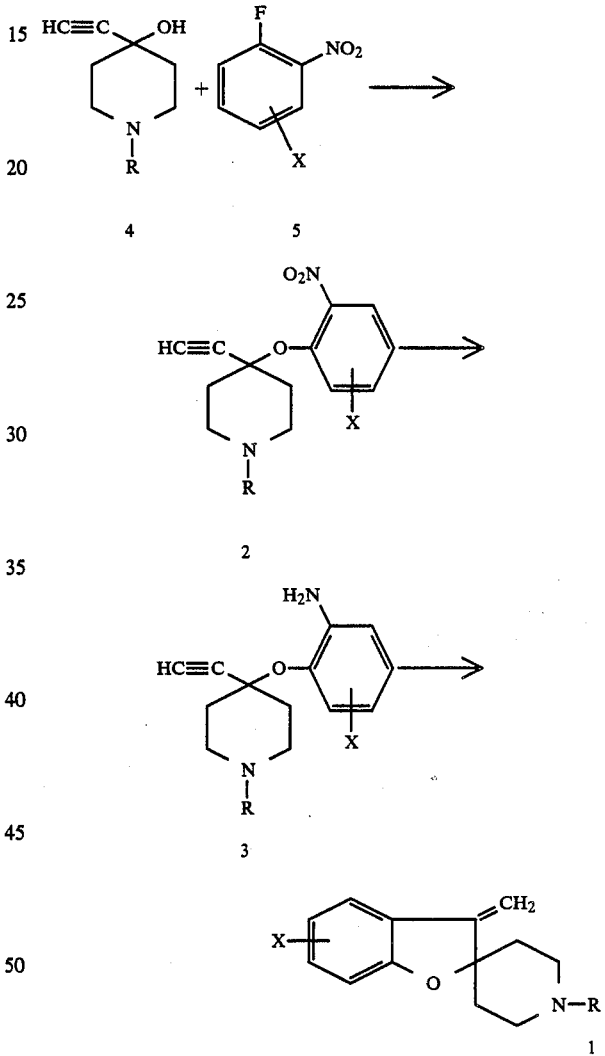

wherein R and X are as hereinbeforedefined.

I claim:
1. A compound of the formula

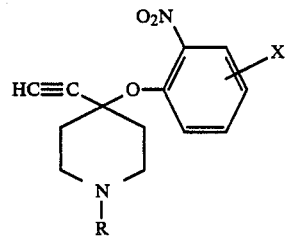

wherein R is hydrogen, loweralkyl of 1 to 6 carbon atoms, a group of the formula

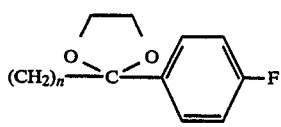

wherein n is 2 or 3, a group of the formula

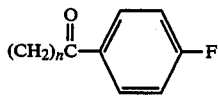

wherein n is 2 or 3, a group of the formula

wherein R¹ is loweralkyl of 1 to 6 carbon atoms or phenyl, or a group of the formula

wherein R² is hydrogen or loweralkyl of 1 to 6 carbon atoms; and X is hydrogen, halogen, loweralkyl of 1 to 6 carbon atoms, loweralkoxy of 1 to 6 carbon atoms, hydroxy or trifluoromethyl, an optical isomer thereof or a salt thereof.

2. A compound of claim 1 wherein R is hydrogen or a group of the formula

and X is halogen.

3. The compound of claim 2 which is 4-ethynyl-4-(2-nitrophenoxy)piperidine.

4. The compound of claim 1 which is 1-methyl-4-ethynyl-4-(2-nitrophenoxy)piperidine.

5. The compound of claim 1 which is 1-methyl-4-ethynyl-4-(4-fluoro-2-nitrophenoxy)piperidine.

6. The compound of claim 1 which is 1-acetyl-4-ethynyl-4-(2-nitrophenoxy)piperidine.

7. The compound of claim 2 which is 1-acetyl-4-ethynyl-4-(4-fluoro-2-nitrophenoxy)piperidine.

8. The compound of claim 1 which is 1-phenoxycarbonyl-4-ethynyl-4-(2-nitrophenoxy)piperidine.

9. The compound of claim 2 which is 1-phenoxycarbonyl-4-ethynyl-4-(4-fluoro-2-nitrophenoxy)piperidine.

10. The compound of claim 2 which is 1-ethoxycarbonyl-4-ethynyl-4-(4-fluoro-2-nitrophenoxy)piperidine.

11. The compound of claim 2 which is 1-{N-3-[2-(4-fluorophenyl)-1,3-dioxolan-2-yl]propyl}-4-ethynyl-4-(2-nitrophenoxy)piperidine.

12. The compound of claim 2 which is 1-[4-(4-fluorophenyl)-4-oxobutyl]-4-ethynyl-4-(2-nitrophenoxy)-piperidine.

13. A compound of the formula

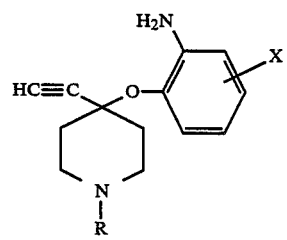

wherein R is loweralkyl of 1 to 6 carbon atoms, a group of the formula

wherein R¹ is loweralkyl of 1 to 6 carbon atoms or phenyl or a group of the formula

wherein R² is hydrogen or loweralkyl of 1 to 6 carbon atoms; X is hydrogen, halogen, loweralkyl of 1 to 6 carbon atoms, loweralkoxy of 1 to 6 carbon atoms, hydroxy or trifluoromethyl, an optical antipode thereof and a salt thereof.

14. A compound of claim 13 wherein R is a group of the formula

and X is halogen.

15. The compound of claim 13 which is 1-methyl-4-(2-aminophenoxy)-4-ethynylpiperidine.

16. The compound of claim 14 which is 1-acetyl-4-(2-amino-4-fluorophenoxy)-4-ethynylpiperidine.

17. The compound of claim 13 which is 1-N-ethoxycarbonyl-4-(2-amino-4-fluorophenoxy)-4-ethynylpiperidine.

18. The compound of claim 13 which is 1-N-phenoxycarbonyl-4-(2-amino-4-fluorophenoxy)-4-ethynylpiperidine.

* * * * *